United States Patent [19]

Drzewiecki et al.

[11] 4,277,971
[45] Jul. 14, 1981

[54] FLUIDIC OIL VISCOMETER

[75] Inventors: Tadeusz M. Drzewiecki, Silver Spring; Richard M. Phillippi, Highland, both of Md.

[73] Assignee: The United States of America as represented by the Secretary of the Army, Washington, D.C.

[21] Appl. No.: 110,958

[22] Filed: Jan. 10, 1980

[51] Int. Cl.³ .................. G01N 11/04; G01N 33/30
[52] U.S. Cl. .................................. 73/55; 137/804
[58] Field of Search .................. 73/54, 55; 137/803, 137/804, 805, 827, 833, 834

[56] References Cited

U.S. PATENT DOCUMENTS

| | | | |
|---|---|---|---|
| 3,616,809 | 11/1971 | Laakaniemi et al. | 137/804 |
| 3,678,733 | 7/1972 | Blatter | 73/54 |
| 3,744,315 | 7/1973 | Hirs | 73/54 X |
| 3,952,576 | 4/1976 | Drzewiecki | 73/54 |
| 4,120,322 | 10/1978 | Bowles | 73/54 X |

Primary Examiner—Gerald Goldberg
Assistant Examiner—Joseph W. Roskos
Attorney, Agent, or Firm—Nathan Edelberg; Robert P. Gibson; Saul Elbaum

[57] ABSTRACT

A fluidic oil viscometer for determining the degradation of machinery lubricating oils compares the viscosity of the machinery oil with the viscosity of another fluid, such as air. Both the viscosity of the air and the viscosity of the oil are sensed, using capillary-orifice combination sensors, and the air viscosity reading is amplified using a series of laminar proportional amplifiers to equalize its change in viscosity with that of oil. The outputs of the capillary orifice combination sensors are applied to two different pressure gauges, the difference between these two pressure gauges represents the viscosity breakdown. This difference will be independent of temperature.

10 Claims, 3 Drawing Figures

FLUIDIC OIL VISCOMETER

RIGHT OF THE GOVERNMENT

The invention described herein may be manufactured, used and licensed by or for the United States Government for Governmental purposes without the payment to us of any royalties thereof.

BACKGROUND OF THE INVENTION

1. Field of the Invention

The present invention relates to a means for determining the degradation of lubricating ability of an oil by detecting the change in viscosity of the oil.

2. Description of the Prior Art

There has long been a need to determine the degradation in the lubricating properties of an oil so that the oil may be changed before the lubricating properties deteriorate to an unacceptable degree. In the past, oil has been changed at regular mileage intervals, so that the lubricating properties may be kept at an acceptable quality. Changes in operating conditions, however, can cause a great difference in the quality of the lubrication ability of oils operated under different conditions.

One known measuring technique is to extract a sample of the oil, and test it in a comercially available viscometer. This process has problems however, due to the fact that the oil must be removed from the vehicle, and tested in an expensive apparatus which is not easily movable.

There exist prior art oil viscometers which test the oil viscosity using a built in capillary-orifice combination viscometer which tests the viscosity of the oil without removing the oil from its environment. However, these viscometers do not compensate for the variations in viscosity due to temperature, and therefore, they are not as accurate as the viscometer of the present invention.

SUMMARY OF THE INVENTION

Accordingly, it is an object of the present invention to provide a way to accurately determine the viscosity of oil without variations due to temperature.

It is a further object of the invention to provide an oil viscometer which measures the change in oil viscosity without being affected by differences in the original viscosity of the oil used.

It is still another object of the present invention to provide an oil viscometer which can measure the change in viscosity of the oil monitored without removal of a sample of the oil from the engine in which the oil is contained.

It is a further object of the present invention to provide a simple oil viscometer which compares the viscosity of oil to standard, which is developed from the viscosity of air.

These, and other objects of the invention are achieved by providing an oil viscometer which measures the viscosity of the oil and then the viscosity of air, which is modified to produce a model of the oil viscosity before use. This modification of the viscosity of air signal into an oil model viscosity signal is done by measuring the viscosity of the oil to be tested before use and amplifying the viscosity of air signal using laminar proportional amplifiers to produce the same viscosity change vs. temperature curve as the fresh oil to be tested. The oil model viscosity signal is then compared to the oil in use to determine the amount of degradation which has occurred to the oil in use. The comparison of these two output signals is done through the use of two separate pressure gauges. One pressure gauge is for measuring the viscosity of the fresh oil model and the other is for measuring the viscosity of the oil being monitored. When fresh oil is added to the engine the measurements of the two gauges are aligned so that they both read the same viscosity. Then, as the oil to be sensed degrades, the viscosity of that oil shown on one of the gauges changes from the viscosity shown on the other gauge, showing the operator that the oil has degraded.

These and other characteristics of the present invention may be better understood in relation to the drawings and the detailed description to follow.

DETAILED DESCRIPTION OF THE INVENTION

Figure 1:
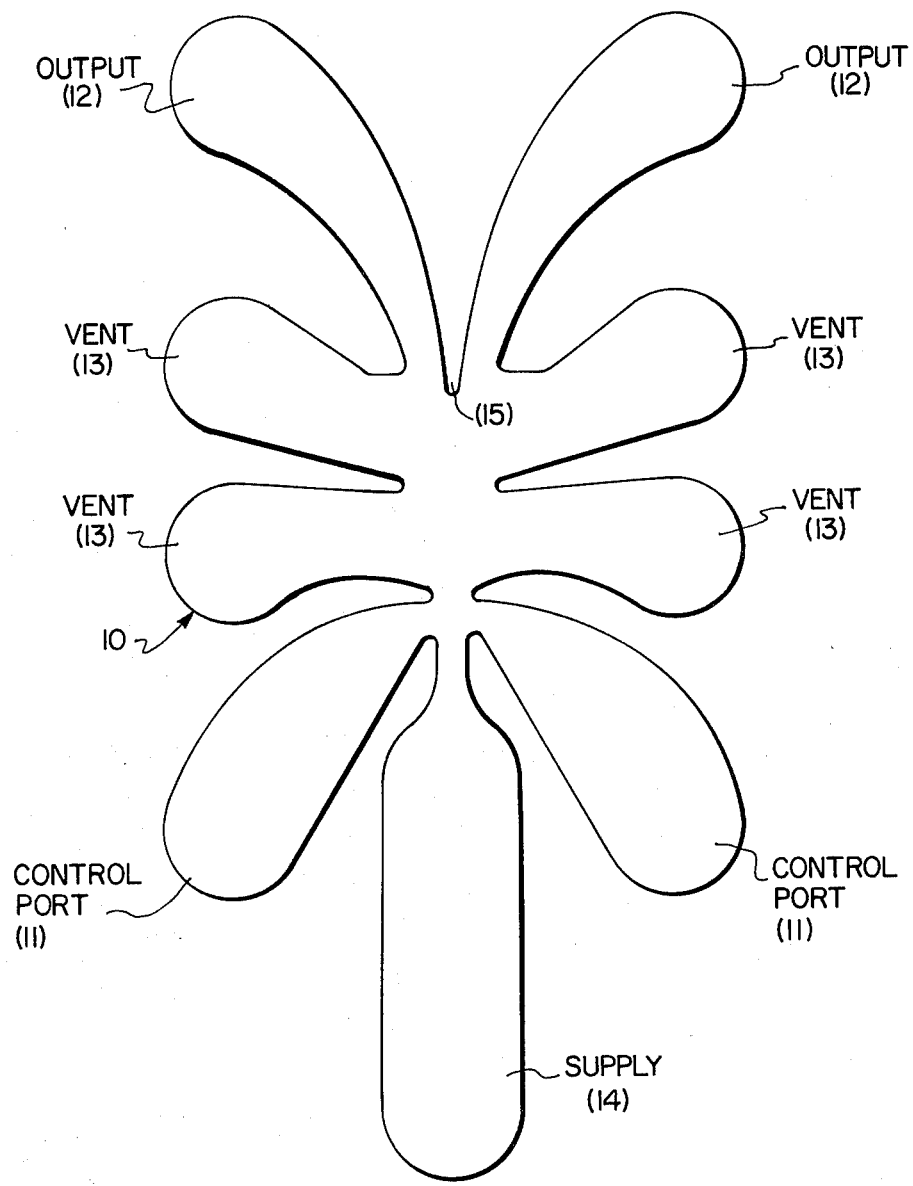
FIG. 1 is a diagrammatic illustration of a typical fluidic laminar proportional amplifier, used in the present invention.

Referring in detail to FIG. 1 which shows a typical fluidic amplifier 10 with control ports 11 representing the signal input ports to the fluidic amplifier, the outputs 12 representing the signal output ports of the amplifier. The vents 13 simply vent the excess fluid which is unable to exit from the output ports 12. In operation, the fluid supply 14 flows in a jet stream towards the splitter 15, symmetrically disposed with respect to outputs 12. If there is no difference in pressure at the control ports 11, there should be no difference in pressure at the output ports 12. The splitter 15 acts as a means for splitting the jet stream equally in two directions in such a way as to create an equal pressure at both outputs. If there is a pressure differential at the control ports 11, then the jet stream will be affected in such a way that the splitter 15 will force a greater amount of flow through one output 12 than the other output 12. This causes the input pressure differential to be amplified so that the output pressure differential is greater than the input pressure differential.

Figure 2:
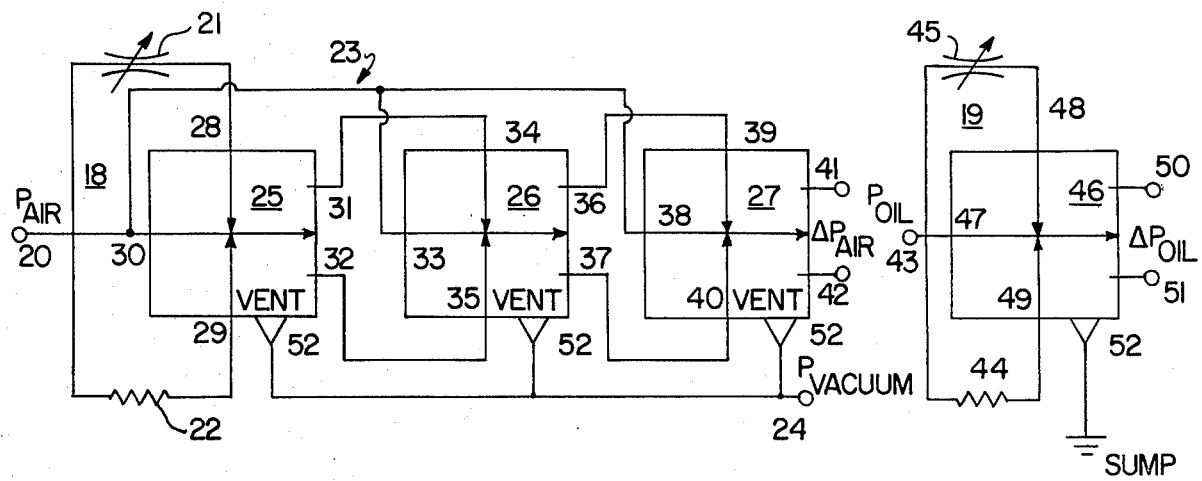
FIG. 2 is a diagrammatic illustration of the fluidic sensor of this application.

In the present invention, two fluidic viscosity sensors at the same temperature and location are used, generally indicated in FIG. 2 as 18, 19. A first air viscosity sensor generally indicated as 18, is representative of capillary-orifice combination fluidic sensors. This air viscosity sensor includes a variable orifice 21, and a capillary sensor 22. When the air pressure is applied to input $P_{air}20$ then any change in viscosity of the air results in a change in the differential pressure at the inputs 28,29 of laminar proportional amplifier 25. The change in differential pressure at the inputs 28, 29 of amplifier 25 is proportional to the change in viscosity of the air. The differential output pressure of this viscosity sensor is input to control terminals 28 and 29 of a laminar proportional amplifier 25. A constant input air pressure Pair is applied to supply terminal 30 of this amplifier, and the pressure differential applied at terminals 28 and 29 is amplifier at terminals 31 and 32. This amplifier pressure differential at 31 and 32 is again applied to the input of a second laminar proportional amplifier 26 and the resulting pressure differential is again amplified at output 36, 37. This process is again repeated in a third amplifier 27 to obtain a resulting output pressure differential across the output terminals 41, 42. Excess air is vented from the amplifiers 25, 26, 27 by the use of vents 52 which return this air to the engine manifold or outside by lines 24.

The oil viscosity sensor 19 is also a capillary-orifice combination sensor and functions in the same manner as air viscosity sensor 18. The viscosity of the oil is monitored using viscosity sensor 19 including variable orifice 45 and capillary sensor 44 whose output is applied to the input terminals of ports 48, 49 of laminar proportional amplifier 46. Excess oil is vented from the amplifier 46 by use of vents 52 to the crankcase sump. The output of this amplifier is indicative of the viscosity of the oil to be measured. The pressure differentials of air viscosity amplifier and of the oil viscosity amplifier are each connected to a separate pressure gauge which reads the viscosity in response to the differential pressure applied across it. Since viscosity of a gas increases with increasing temperature and the viscosity of a liquid decreases as a function of increasing temperature, it is necessary to reverse the differential output polarity of the air viscosity amplifier output.

The variable orifices of the air and oil sensors can be adjusted to allow the matching of the two sensors when different weights of oil and/or fresh oil is added. This adjustment is done to align the viscosity values of the two gauges when the oil to be monitored is fresh. Because of the differences between the change in the viscosity vs. the change in the temperature of air and oil, more gain is necessary in the air sensor to equalize these changes. This is necessary because a change in temperature will change the viscosity of air. For a 0°–200° F. change in temperature, the change in viscosity of oil over the change in viscosity in air is approximately equal to 230, thus requiring that the air powered unit reflect this ratio in additional gain. This gain of 230 is obtainable using the three stages of amplification provided by amplifiers 25, 26, 27. Once properly matched, the viscosity versus temperature for the fresh oil and the air standard will be equivalent for the same batch of oil.

Figure 3:
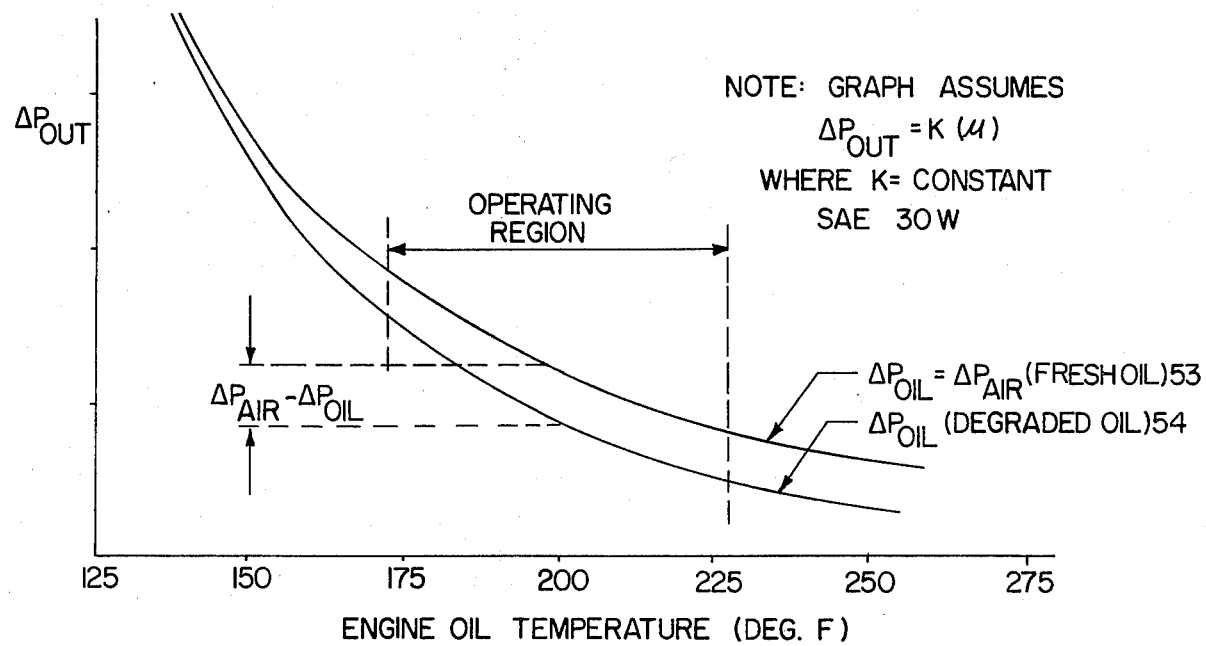
FIG. 3 is a graph showing the viscosity oil temperature characteristics of the oil and air used in the present invention.

FIG. 3 shows the viscosity of oil versus engine oil temperature when fresh engine oil is matched to the viscosity of the output of the air standard. In this case, when the oil has degraded, the viscosity of the oil increases, decreasing the pressure differential and the resultant differential pressure output of the laminar proportional amplifier 46 that has the oil input applied. This is shown in curve 54. The distance between the two curves is proportional to the viscosity change at a given temperature.

The pressure transducers used for indicating the viscosity of the oil can easily be engine mounted, or mounted on the dashboard thus eliminating the need for motor pool inspection or sampling of the oil in the crankcase.

It is noted that various modifications may be made to this invention, these modifications limited only by the necessity for matching the viscosity of air with the viscosity of fresh oil.

We wish it to be understood that we do not desire to be limited to the exact detail of construction shown and described for obvious modifications can be made by persons skilled in the art.

We claim:

1. A method of detecting the change in viscosity of a first fluid independent of temperature including means for measuring the viscosity of the first fluid to be monitored relative to the viscosity of a second fluid including the steps of:

calibrating the means for measuring so that the viscosity vs. temperature curve of the first fluid is substantially the same as the viscosity vs. temperature curve of the second fluid; and monitoring the relative change in viscosity of the monitored fluid by the difference between the two fluid viscosities such that the relative change in viscosity is independent of temperature.

2. A fluidic viscometer for detecting the change in viscosity of a first fluid to be monitored independent of temperature comprising:

first means for measuring the viscosity of the first fluid to be monitored;

second means for measuring the viscosity of a second fluid;

means for calibrating said first or second means for measuring so that the viscosity vs. temperature curve of the first fluid is substantially the same as the viscosity vs. temperature curve of the second fluid; and means for monitoring the relative change in viscosity of the monitored fluid using the difference between the two fluid viscosities such that the relative change in viscosity is independent of temperature.

3. The fluid viscometer of claim 2, wherein said first means for measuring the viscosity of the first fluid to be monitored includes a capillary-orifice combination viscometer sensor means.

4. The fluidic viscometer of claim 2, wherein said second means for measuring the viscosity of a second fluid includes a capillary-orifice combination viscometer sensor means.

5. The fluidic viscometer according to claim 2, wherein said means for calibrating includes at least one laminar proportional amplifier means for amplifying the output of one of said capillary-orifice combination viscometer sensor means.

6. The fluidic viscometer of claim 2, wherein said means for monitoring the relative change in viscosity includes a pair of pressure gauge means; and wherein the change in viscosity of the monitored fluid is determined by a visual inspection of the pair of pressure gauge means.

7. The fluidic viscometer of claim 3, wherein the output of said first means for measuring the viscosity of the first fluid to be monitored is a differential pressure.

8. The fluidic viscometer of claim 4, wherein the output of said second means for measuring the viscosity of the second fluid is a differential pressure.

9. The oil viscometer of claim 5, wherein said means for calibrating inverts the output of one of said capillary-orifice combination viscometer means with respect to the output of the other capillary-orifice combination viscometer sensor means.

10. The oil viscometer of claim 2, wherein the first fluid to be monitored is oil, and wherein the second fluid is air.

* * * * *